US00PP30671P2

(12) United States Plant Patent
Furuta

(10) Patent No.: US PP30,671 P2
(45) Date of Patent: Jul. 9, 2019

(54) ***DIANTHUS* PLANT NAMED 'MIDTEMARI'**

(50) Latin Name: *Dianthus barbatus*
Varietal Denomination: Midtemari

(71) Applicant: MIYOSHI & Co., Ltd., Tokyo (JP)

(72) Inventor: Jyoji Furuta, Wakayama (JP)

(73) Assignee: Miyoshi & Co., Ltd., Tokyo (JP)

( * ) Notice: Subject to any disclaimer, the term of this patent is extended or adjusted under 35 U.S.C. 154(b) by 0 days.

(21) Appl. No.: 15/932,647

(22) Filed: Mar. 30, 2018

(51) Int. Cl.
*A01H 5/02* (2018.01)

(52) U.S. Cl.
USPC ..... Plt./273

(58) Field of Classification Search
USPC ..... Plt./273
See application file for complete search history.

(56) References Cited

U.S. PATENT DOCUMENTS

| | | | |
|---|---|---|---|
| 509,707 | A | 11/1893 | Vachon |
| 1,072,594 | A | 9/1913 | Ferrara |
| 1,205,808 | A | 11/1916 | Steele |
| 1,225,623 | A | 5/1917 | Hall et al. |
| 1,507,189 | A | 9/1924 | Keyes |
| 1,806,162 | A | 5/1931 | Hahn |
| 2,254,579 | A | 9/1941 | Okie |
| 3,296,669 | A | 1/1967 | Elder, Jr. |
| 3,358,338 | A | 12/1967 | Classen |
| 3,473,198 | A | 10/1969 | Meier |
| 4,290,172 | A | 9/1981 | Burton |
| 4,884,321 | A | 12/1989 | Holub |
| 5,119,539 | A | 6/1992 | Curry |
| 5,158,428 | A | 10/1992 | Gessner et al. |
| 5,572,778 | A | 11/1996 | Stenner et al. |
| 6,473,944 | B1 | 11/2002 | Vazin |
| 6,546,601 | B1 | 4/2003 | Kawashima |
| 6,725,575 | B2 | 4/2004 | Curel |
| 7,143,486 | B2 | 12/2006 | Rolla |
| D614,855 | S | 5/2010 | Inchara et al. |
| 7,806,909 | B2 | 10/2010 | Fallin et al. |
| 8,388,655 | B2 | 3/2013 | Fallin et al. |
| 2006/0190041 | A1 | 8/2006 | Fallin et al. |

OTHER PUBLICATIONS

PLUTO Plant Variety Database Jan. 8, 2019.*

* cited by examiner

*Primary Examiner* — Annette H Para
(74) *Attorney, Agent, or Firm* — C. A. Whealy

(57) ABSTRACT

A new and distinct cultivar of *Dianthus* plant named 'Midtemari', characterized by its compact and upright plant habit; moderately vigorous growth habit; moderately strong flower stems; early flowering habit; large flowers fully covered with numerous bright green-colored bracts; and good container and garden performance.

2 Drawing Sheets

Botanical designation: *Dianthus barbatus.*
Cultivar denomination: 'MIDTEMARI'.

BACKGROUND OF THE INVENTION

The present invention relates to a new and distinct cultivar of *Dianthus* plant, botanically known as *Dianthus barbatus*, grown commercially as a container and/or garden plant and hereinafter referred to by the name 'Midtemari'.

The new *Dianthus* plant is a naturally-occurring whole plant mutation of *Dianthus barbatus* 'Temarisou', not patented. The new *Dianthus* plant was discovered and selected by the Inventor on Mar. 10, 2015 as a single plant from within a population of plants of 'Temarisou' in a controlled greenhouse environment in Hidakagun, Wakayama, Japan.

Asexual reproduction of the new *Dianthus* plant by in vitro meristem culture propagated in a controlled environment in Kobuchizawa, Yamanashi, Japan since Oct. 1, 2016 has shown that the unique features of this new *Dianthus* plant are stable and reproduced true to type in successive generations of asexual reproduction.

SUMMARY OF THE INVENTION

Plants of the new *Dianthus* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Midtemari'. These characteristics in combination distinguish 'Midtemari' as a new and distinct *Dianthus* plant:

1. Compact and upright plant habit.
2. Moderately vigorous growth habit.
3. Moderately strong flower stems.
4. Early flowering habit.
5. Large flowers with numerous bright green-colored bracts.
6. Good container and garden performance.

Plants of the new *Dianthus* differ primarily from plants of the mutation parent, 'Temarisou', in the following characteristics:

1. Plants of the new *Dianthus* are more compact than plants of 'Temarisou'; additionally, plants of 'Temarisou' are more suitable as a cut flower rather than a container or garden plant.
2. Plants of the new *Dianthus* flower about one month earlier than plants of 'Temarisou'.

Plants of the new *Dianthus* can be compared to plants of *Dianthus barbatus* 'Breagreen', disclosed in U.S. Plant Pat. No. 25,026. In side-by-side comparisons, plants of the new *Dianthus* differ primarily from plants of 'Breagreen' in the following characteristics:

1. Plants of the new *Dianthus* are more compact and less vigorous than plants of 'Breagreen'; additionally, plants of 'Breagreen' are more suitable as a cut flower rather than a container or garden plant.
2. Leaves of plants of the new *Dianthus* are lighter green in color than leaves of plants of 'Breagreen'.
3. Plants of the new *Dianthus* flower about one month earlier than plants of 'Breagreen'.

BRIEF DESCRIPTION OF THE PHOTOGRAPHS

The accompanying photographs illustrate the overall appearance of the new *Dianthus* plant showing the colors as true as it is reasonably possible to obtain in colored reproductions of this type. Colors in the photographs may differ slightly from the color values cited in the detailed botanical description which accurately describe the colors of the new *Dianthus* plant.

The photograph on the first sheet is a side perspective view of a typical plant of 'Midtemari'.

The photograph on the second sheet is a close-up view of a typical flower of 'Midtemari'.

DETAILED BOTANICAL DESCRIPTION

Plants used in the aforementioned photographs and following observations and measurements describe plants grown during the spring and summer in 10.5-cm containers in a glass-covered greenhouse in Hokuto-City, Yamanashi, Japan and under cultural practices typical of commercial container *Dianthus* production. During the production of the plants, day temperatures averaged 25° C., night temperatures averaged 20° C. and light levels averaged 80,000 lux. Plants were 13 weeks old when the photographs and description were taken. In the following description, color references are made to The Royal Horticultural Society Colour Chart, 2007 Edition, except where general terms of ordinary dictionary significance are used.

Botanical classification: *Dianthus barbatus* 'Breagreen'.

Parentage: Naturally-occurring whole plant mutation of *Dianthus barbatus* 'Temarisou', not patented.

Propagation:

*Type*.—By in vitro meristem cuttings.

*Time to initiate roots, summer*.—About three weeks at ambient temperatures ranging from 20° C. to 30° C. and soil temperature about 20° C.

*Time to initiate roots, winter*.—About three weeks at ambient temperatures ranging from 12° C. to 20° C. and soil temperature about 20° C.

*Time to produce a rooted young plant, summer*.—About five weeks at ambient temperatures ranging from 20° C. to 30° C. and soil temperature about 20° C.

*Time to produce a rooted young plant, winter*.—About six weeks at ambient temperatures ranging from 12° C. to 20° C. and soil temperature about 20° C.

*Root description*.—Fine, fibrous; typically close to 155C in color.

*Rooting habit*.—Moderate branching; medium density.

Plant description:

*Plant and growth habit*.—Herbaceous perennial; compact and upright plant form with moderately strong flowering stems; narrow inverted triangle; moderately vigorous growth habit.

*Branching habit*.—Basal-branching growth habit, about five to seven flowering stems develop per plant.

*Plant height*.—About 20 cm.

*Plant diameter or spread*.—About 25 cm.

*Flowering stems*.—Length: About 20 cm. Diameter: About 5 mm. Internode length: About 5 cm. Strength: Moderately strong. Texture and luster: Smooth, glabrous; matte. Color: Close to 143A; at the nodes, close to 143B.

*Leaf description*.—Arrangement: Opposite, simple; sessile. Length: About 1.9 cm to 9 cm. Width: About 1.4 cm to 6 cm. Shape: Lanceolate. Apex: Obtuse. Base: Long cuneate, decurrent. Margin: Entire. Texture and luster, upper and lower surfaces: Smooth, glabrous; matte. Venation pattern: Parallel. Color: Developing leaves, upper and lower surfaces: Close to 143C. Fully expanded leaves, upper surface: Close to 137A; venation, close to 137A. Fully expanded leaves, lower surface: Close to 137C; venation, close to 137C.

Flower description:

*Flower type and flowering habit*.—Single, almost spherical, terminal flowers without floral structures typical of *Dianthus* plants; flower head fully covered with sepals and modified bracts.

*Natural flowering season*.—Flowering is continuous through the summer into the autumn in Japan; early flowering habit, plants begin flowering about ten weeks after planting.

*Flower longevity*.—Good postproduction longevity with flowers lasting about 30 days on the plant; flowers persistent.

*Petals*.—None observed to date.

*Sepals*.—Quantity per flower: About 80. Length: About 1.6 cm. Width: About 1 cm. Shape: Lanceolate. Apex: Long acuminate. Base: Cuneate. Margin: Entire. Texture and luster, upper and lower surfaces: Smooth, glabrous; matte. Color: When opening, upper and lower surfaces: Close to 143C. Fully opened, upper and lower surfaces: Close to 143B; color does not change with subsequent development.

*Bracts*.—Quantity per flower: About 102. Length: About 1.7 cm. Width: About 3 mm. Shape: Lanceolate. Apex: Long acuminate. Base: Cuneate. Margin: Entire. Texture and luster, upper and lower surfaces: Smooth, glabrous; matte. Color: When opening, upper and lower surfaces: Close to 143C. Fully opened, upper and lower surfaces: Close to 143C; color does not change with subsequent development.

*Reproductive organs*.—None observed to date.

*Fruits and seeds*.—None observed to date.

Disease & pest resistance: Plants of the new *Dianthus* have not been observed to be resistant to pathogens and pests common to *Dianthus* plants to date.

Garden performance: Plants of the new *Dianthus* have been observed to have good garden performance, to tolerate rain and to tolerant to temperatures ranging from 5° C. to 30° C.

It is claimed:

1. A new and distinct *Dianthus* plant named 'Midtemari' as illustrated and described.

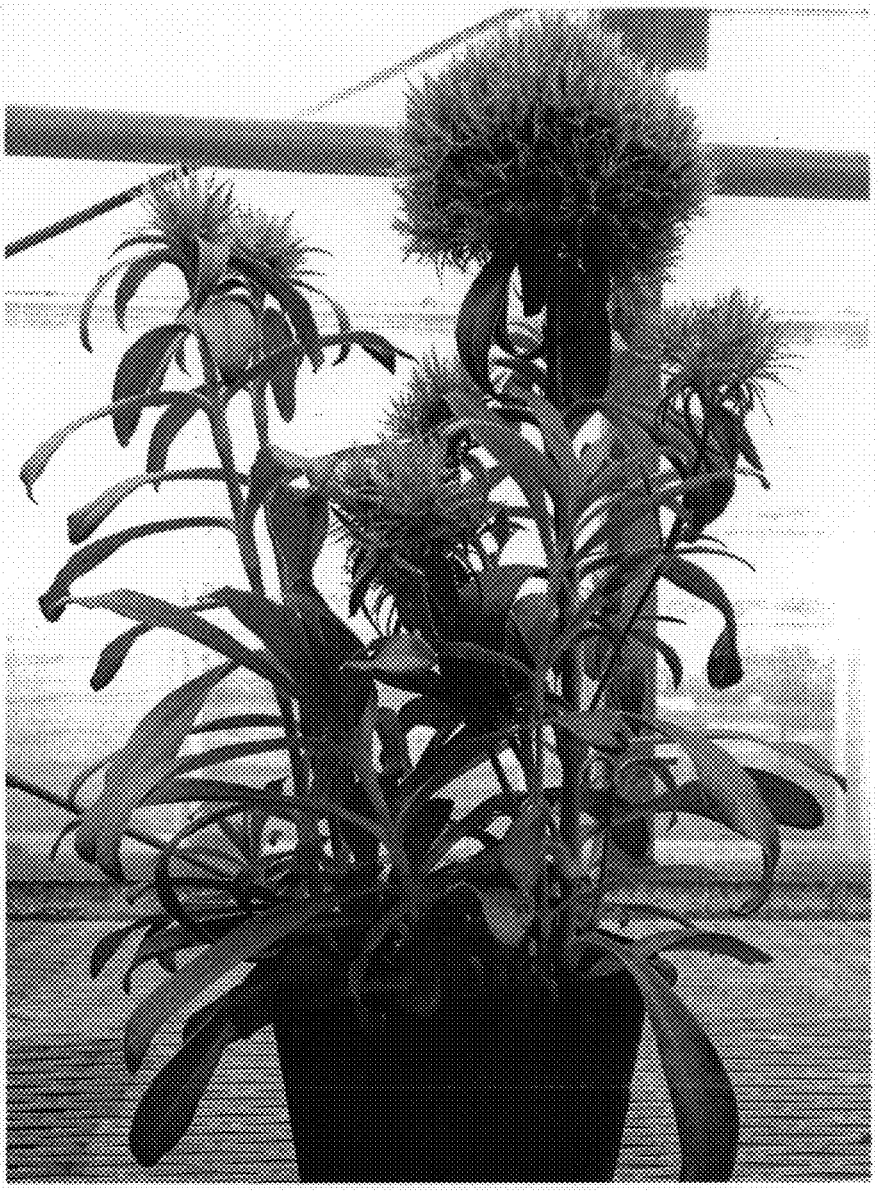

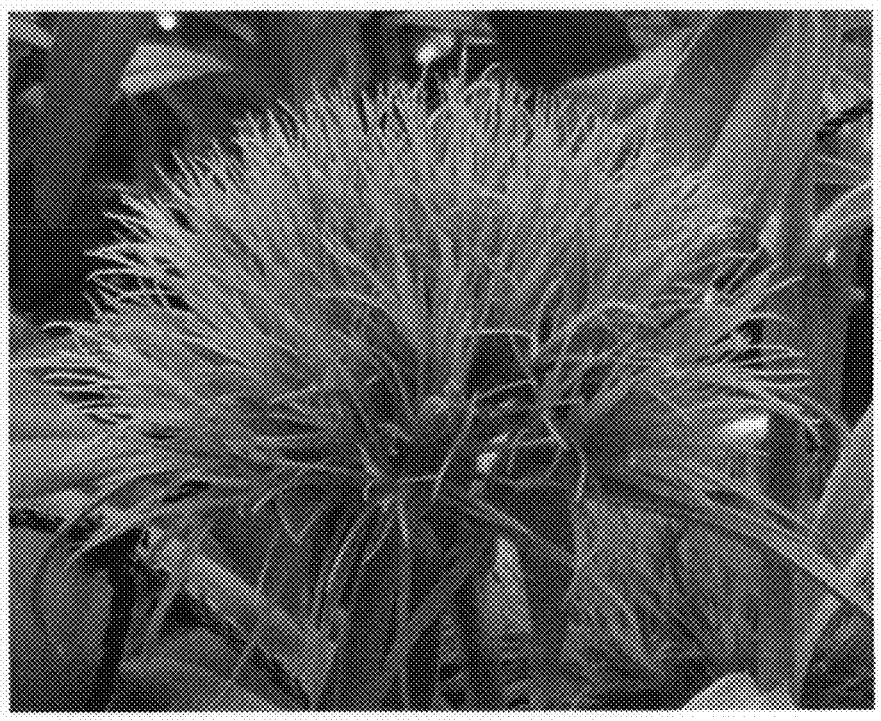

* * * * *